United States Patent [19]
Balogh et al.

[11] Patent Number: 5,889,018
[45] Date of Patent: Mar. 30, 1999

[54] HETEROCYCLIC COMPOUNDS, PHARMACEUTICAL COMPOSITIONS COMPRISING THEM AND PROCESS FOR THE PREPARATION THEREOF

[75] Inventors: Gyula Balogh, deceased, late of Budapest, by Erzsébet Láposi, executrix; Imre Domán, Budapest; Gábor Blaskó, Budapest; Gyula Simig, Budapest; Erzsébet Kovács née Kaszab, Budapest; István Gyertyán, Budapest; András Egyed, Budapest; István Gacsályi, Budapest; András Bilkei-Gorzó, Budapest; Katalin Pallagi, Budapest; Katalin Szemerédi, Budapest; Klára Kazó née Daróczi, Budapest, all of Hungary

[73] Assignee: Egis Gyogyszergyar RT., Budapest, Hungary

[21] Appl. No.: 433,120

[22] Filed: May 3, 1995

[30]     Foreign Application Priority Data

May 3, 1994 [HU]   Hungary .............................. P 94 01281

[51] Int. Cl.⁶ ........................... A61K 31/44; A61K 31/47
[52] U.S. Cl. ........................................... 514/291; 514/307
[58] Field of Search ..................... 546/149, 90; 514/307, 514/291

[56]          References Cited

FOREIGN PATENT DOCUMENTS 71110   2/1970   German Dem. Rep. .
71110  11/1970   German Dem. Rep. .

*Primary Examiner*—Matthew V. Grumbling
*Assistant Examiner*—Bruck Kifle
*Attorney, Agent, or Firm*—Beveridge, DeGrandi Weilacher & Young, L.L.P.

[57]          ABSTRACT

The invention relates to anxiolytic pharmaceutical compositions comprising as active ingredient 1-sytrylisoquinoline derivatives of general formula (I), wherein n is 1, 2, 3 or 4;

R may be the same or different and represent(s) hydrogen, lower alkyl, lower alkoxy or hydroxy, or two substituents R attached to adjacent carbon atoms may form together an alkylenedioxy group;

$R^1$ represents hydrogen or lower alkyl, and

Ar stands for an optionally substituted aryl or heteroaryl,

Some of the compounds of general formula (I) is known, but the majority thereof has not so far described in the literature.

The invention also encompasses the preparation of the new compounds of general formula (I), which comprises reacting a compound of general formula (II) with an aldehyde or general formula (III) in the presence of a condensing agent or an acidic catalyst.

2 Claims, No Drawings

HETEROCYCLIC COMPOUNDS, PHARMACEUTICAL COMPOSITIONS COMPRISING THEM AND PROCESS FOR THE PREPARATION THEREOF

This invention relates to new heterocyclic compounds, a process for the preparation thereof, pharmaceutical compositions comprising the same, to the use of the said heterocyclic compounds for the treatment of diseases and for the preparation of pharmaceutical compositions suitable for the treatment of diseases. More specifically, the invention relates to 1-styrylisoquinoline derivatives and a process for the preparation thereof and pharmaceutical compositions having particularly an anxiolytic activity containing as active ingredient new 1-styrylisoquinoline derivatives.

A great number of 1-styrylisoquinoline derivatives and the pharmaceutical activities thereof are known in the literature. Processes for the preparation of this group of compounds have also been described. In the German patent specification No. 576,232 a synthesis for the preparation of 6,7-dialkoxy-1-styrylisoquinolines exerting spasmolytic and analgetic effects is provided. The synthesis routes well-known from the isoquinoline chemistry are illustrated by the reaction scheme I. According to the synthesis 6,7-dialkoxy-1-styrylisoquinolines can be prepared by condensing an appropriate 1-methylisoquinoline of formula (A) with an aldehyde of general formula ArCHO. The condensation of the appropriate 1-methyl-3,4-dihydroisoquinoline and aldehyde of the formula ArCHO results in the appropriate 1-styryl-3,1-dihydroisoquinolines of general formula (C). The latter compounds can also be prepared by subjecting the acylated amines of general formula (E) obtained from the appropriate 2-aryl-ethylamines of general formula (D) to a cyclization reaction of Bischler-Napieralski type. Furthermore, the 1-styrylisoquinolines can be produced by a catalytic dehydrogenation of the 1-styryl-3,4-dihydroisoquinolines of general formula (C).

According to the published German patent application No. 1,902,402 6,7-dimethoxy-1-styrylisoquinolines are produced by the above process. It is also mentioned that the said compounds inhibit the platelet functions (e.g. adhesion, agglomeration and retraction) and the liberation of biogenous amines from the amine-storing cells.

Some 1-styrylisoquinoline derivatives can also be prepared from appropriately acylated 2-aryl-2-alkoxyethylamines by a cyclization reaction of Bischler-Napieralski type [J. Knabe, H. D. Höltje: Arch. Pharm. 303, 404 (1970)].

The aim of the present invention was to provide pharmaceutically active new 1-styrylisoquinoline derivatives, furthermore to enlarge the pharmaceutical applicability of the hitherto known l-styrylisoquinolines and to reveal new fields of indications.

According to an aspect of the present invention there are provided new heterocyclic compounds of general formula (I), wherein n is 1, 2, 3 or 4, R may be the same or different and represent(s) hydrogen, lower alkyl, lower-alkoxy or hydroxy, or two substituents R attached to adjacent carbon atoms may form together an alkylenedioxy group;

$R^1$ represents hydrogen or lower alkyl, and

Ar stands for an optionally substituted aryl or heteroaryl, except the following compounds:

6,7-dimethoxy-1-(3,4-dimethoxystyryl)-isoquinoline;
6,7-dimethoxy-1-(3,4-methylenedioxystyryl)-isoquinoline;
6,7-dimethoxy-1-(3,4,5-trimethoxystyryl)-isoquinoline;
6,7-dimethoxy-1-(3-methoxy-4-hydroxystyryl)-isoquinoline;
6,7-dimethoxy-1-(3-hydroxy-4-methoxystyryl)-isoquinoline;
6,7-dimethoxy-1-(4-chlorostyryl)-isoquinoline;
6,7-dimethoxy-1-styrylisoquinoline;
6,7-methylenedioxy-1-(3,,4-dimethoxystyryl)-isoquinoline;
6,7-methylenedioxy-1-(3,4-methylenedioxstyryl)-isoquinoline;
6,7-dimethoxy-3-methyl-1-(4-chlorostyryl)-isoquinoline;
6,7-dimethoxy-3-methyl-1-(3,4-dimethoxystyryl)-isoquinoline;
6,7-dimethoxy-3-methyl-1-(3,4-methylenedioxystyryl)-isoquinoline, and
6,7-dimethoxy-1-([2-/3-pyridyl/-ethenyl]-isoquinoline).

A preferred group of the compounds of general formula (I) can be characterized by the general formula (IA), wherein $R^1$ stands for hydrogen or lower alkyl;

$R^2$ represents hydrogen;

$R^3$ and $R^4$ each represent hydrogen or lower alkoxy, or together form a lower alkylenedioxy group;

$R^5$ represents hydrogen or lower alkoxy, and

Ar denotes phenyl optionally carrying one or more identical or different substituent(s) selected from the group consisting of halogen, trihalomethyl, hydroxy, lower alkyl, lower alkoxy, lower alkylenedioxy, cyano, nitro, amino, mono- and di-(lower alkyl)-amino; or naphtyl optionally carrying the above-mentioned substituents, or mono- or bicyclic heteroaryl containing one or two oxygen, nitrogen and/or sulfur atom(s).

The term "lower" used throughout the specification and claims designates groups containing 1 to 7 (preferably 1 to 4) carbon atom(s) The term "lower alkyl", refers to straight-chained or branched saturated hydrocarbon groups having 1 to 7, preferably 1 to 4 carbon atom(s) (e.g. methyl, ethyl, n-propyl, isopropyl, n-butyl etc.). The term "lower alkoxy" relates to alkyl ether groups wherein the term "alkyl" corresponds to the above definition (e.g. methoxy, ethoxy, n-propoxy, isopropoxy, n-butoxy etc.). The "lower alkylenedioxy group" relates to groups of the formula —O—(CH$_2$)$_m$—O—, wherein m is 1, 2, 3 or 4 (e.g. methylenedioxy, ethylenedioxy, propylenedioxy etc).

The term "halogen" encompasses all the four halogen atoms, such as fluorine, chlorine, bromine and iodine. Preferred representatives of the "halomethyl groups" are the trifluoromethyl or trichloromethyl groups, particularly the trifluoromethyl group. The term "mono or di-(lower alkyl)-amino" denotes amino groups substituted by one or two, identical or different alkyl group(s) corresponding to the above definition (e.g. methylamino, ethylamino, dimethylamino, diethylamino, methylethylamino, diisopropylamino etc.).

The term "heteroaryl" relates to optionally substituted mono- or bicyclic heteroaryl groups containing one or two oxygen, nitrogen and/or sulfur atom(s), such as furyl, thienyl, pyrrolyl, pyridyl, pyrazinyl, pyridazinyl, oxazolyl, isoxazolyl, thiazolyl, isothiazolyl, pyrimidyl, quinolyl, isoquinolyl etc. As heteroaryl group particularly a pyridyl group (especially the 2-pyridyl or 3-pyridyl), a furyl group (especially the 2-furyl) or a thienyl group (especially the 1- or 2-thienyl) is mentioned.

The pharmaceutically suitable acid addition salts of the compounds of general formula (I) might be salts prepared with inorganic or organic acids (e.g. hydrogen chloride, hydrogen bromide, nitric, sulfuric, phosphoric, maleic, fumaric, nicotinic, citric, malic, lactic, acetic, formic, methanesulfonic, p-toluenesulfonic acid etc.).

Surprisingly it has been found that the compounds of general formula (I) and the salts thereof, wherein n is 1, 2, 3 or 4;

R may be the same or different and represent(s) hydrogen, lower alkyl, lower alkoxy or hydroxy, or two substituents R attached to adjacent carbon atoms may form together an alkylenedioxy group;

$R^1$ represents hydrogen or lower alkyl, and

Ar stands for an optionally substituted aryl or heteroaril; exhibit valuable anxiolytic properties, To a particularly valuable group of the compounds of general formula (IA) belong the compounds wherein $R^1$ stands for hydrogen or methyl;

$R^2$ represents hydrogen;

$R^3$ and $R^4$ each represent methoxy or together form methylenedioxy;

$R^5$ denotes hydrogen or methoxy; and

Ar stands for phenyl carrying a substituent selected from the group consisting of halogen, trifluoromethyl, nitro, methoxy, cyano or methylenedioxy.

Particularly preferred representatives of substituent Ar are phenyl carrying a single substituent in position 4, or phenyl bearing a methylenedioxy substituent in positions 3 and 4, or 3,4-dimethoxyphenyl. The phenyl being in the place of Ar is preferably 4-(trifluoromethyl)-phenyl, 4-nitrophenyl, 4-fluorophenyl, 3,4-dimethoxyphenyl, 4-cyanophenyl or 4-methoxyphenyl, especially 4-(trifluoromethyl)-phenyl, 4-fluorophenyl or 3,4-dimethoxyphenyl.

Valuable representatives of the compounds of general formula (IA) are the following derivatives:
3-methyl-6,7-dimethoxy-1-(4-nitrostyryl)-isoquinoline;
6,7-dimethoxy-1-[4-(trifluoromethyl)-styryl]-isoquinoline;
1-(4-cyanostyryl)-3-methyl-6,7,8-trimethoxyisoquinoline; and
6,7-dimethoxy-1-(4-methoxystyryl)-isoquinoline.

The following representatives of the compounds of general formula (IA) possess particularly valuable pharmaceutical activity:
1-(4-fluorostyryl)-6,7-dimethoxyisoquinoline;
1-(3,4-dimethoxystyryl)-6,7-methylenedioxyisoquinoline, and pharmaceutically acceptable acid addition salts thereof.

Outstanding representatives of the compounds of general formula (IA) are 6,7-methylenedioxy-1-[(4-trifluoromethyl)-styryl]-isoquinoline and pharmaceutically acceptable acid addition salts thereof.

According to a further aspect of the present invention there is provided a process for the preparation of new 1-styrylisoquinoline derivatives of general formula (I), wherein n is 1, 2, 3 or 4, R may be the same or different and represent(s) hydrogen, lower alkyl, lower alkoxy or hydroxy, or two substituents R attached to adjacent carbon atoms may form together an alkylenedioxy group;

$R^1$ represents hydrogen or lower alkyl, and

Ar stands for an optionally substituted aryl or heteroaryl, except the following compounds:
6,7-dimethoxy-1-(3,4-dimethoxystyryl)-isoquinoline;
6,7-dimethoxy-1-(3,4-methylenedioxystyryl)-isoquinoline;
6,7-dimethoxy-1-(3,4,5-trimethoxystyryl)-isoquinoline;
6,7-dimethoxy-1-(3-methoxy-4-hydroxystyryl)-isoquinoline;
6,7-dimethoxy-1-(3-hydroxy-4-methoxystyryl)-isoquinoline;
6,7-dimethoxy-1-(4-chlorostyryl)-isoquinoline;
6,7-dimethoxy-1-styrylisoquinoline;
6,7-methylenedioxy-1-(3,4-dimethoxystyryl)-isoquinoline;
6,7-methylenedioxy-1-(3,4-methylenedioxystyryl)-isoquinoline;
6,7-dimethoxy-3-methyl-1-(4-chlorostyryl)-isoquinoline;
6,7-dimethoxy-3-methyl-1-(3,4-dimethoxystyryl)-isoquinoline;
6,7-dimethoxy-3-methyl-1-(3,4-methylenedioxystyryl)-isoquinoline, and
6,7-dimethoxy-1-([2-/3-pyridyl/-ethenyl]-isoquinoline), and pharmaceutically acceptable acid addition salts thereof, which comprises reacting a compound of general formula (II) with an aldehyde of general formula (III) in the presence of a condensing agent or an acidic catalyst, and optionally converting the thus-obtained compound of general formula (I) into a pharmaceutically acceptable acid addition salt thereof, or liberating a base of general formula (I) from its salt (in the general formulae (II) and (III) R, n, $R^1$ and Ar are as stated above).

According to a preferred embodiment of the process according to the invention the compounds of general formula (IA) are prepared by reacting a compound of general formula (IIA) with an aldehyde of general formula (III) in the presence of a condensing agent or an acidic catalyst, and optionally converting the thus-obtained compound of general formula (IA) into a pharmaceutically acceptable acid addition salt thereof, or liberating a base of general formula (IA) from a salt thereof (in the formulae $R^1$, $R^2$, $R^3$, $R^4$, $R^5$ and Ar are as stated above).

As condensing agent preferably zinc chloride, phosphorus pentoxide, acetic anhydride or propionic anhydride can be used. The reaction is carried out at a temperature between 60° C. and 180° C., preferably between 150° C. and 160° C. The reaction time varies between 1 hour and 8 hours. Generally 0,5–2 mole(s), preferably 1,05–1,2 mole of aldehyde of general formula (III) is applied related to 1 mole of the compound of general formula (II). The reaction mixture can be worked up by methods known per se. It can be preferable to cool the reaction mixture (preferably to a temperature between 0° C. and 10° C.), to precipitate the desired compound with an appropriate solvent (e.g. an ester, such as ethyl acetate, or an ether, such as diethylether) and to filter, wash and dry the separated product.

One can also proceed by carrying out the condensation of the compounds of general formulae (II) and (III) in the presence of an acidic catalyst. For this purpose lower monocarboxylic acids, preferably acetic acid can be used. The reaction can be carried out at a temperature between 60° C. and 150° C., preferably at the boiling point of the reaction mixture. The reaction time varies between 1 hour and 8 hour(s). Generally 0,5 to 2 mole, preferably 1,05 to 1,2 mole of aldehyde of general formula (III) is used related to 1 mole of the compound of general formula (II). The reaction mixture can be worked up by methods known per se. It can be preferable to cool the reaction mixture, add an appropriate solvent (e.g. a ketone, such as acetone) to it and make the mixture strongly acidic. In such cases the separating salt is isolated (e.g. by filtration), then it is washed and dried.

The thus-obtained compound of general formula (I) is obtionally converted into a pharmaceutically acceptable acid addition salt thereof. The salt formation can be carried out by known methods, reacting the compound of general formula (I) with an appropriate acid. A compound of general formula (I) can optionally be liberated from a salt thereof by methods known per se. The process is carried out by reacting the appropriate salt with a preferably inorganic base (e.g. alkali hydroxides, such as sodium hydroxide or potassium hydroxide).

The compounds of general formula (I) possess valuable anxiolytic properties. This recognition is surprising, since such an activity has not so far been attributed to the known 1-styrylisoquinoline derivatives in the technical literature. It has been found that the compounds of general formula (I) exhibit an outstandingly strong anxiolytic activity, which surpasses by orders of magnitude that of the hitherto known therapeutical agents. A further advantage of the compounds of general formula (I) is that they are only slightly toxic.

The activity of the compounds of general formula (I) is shown by the following tests:

I. Acute Toxicity

White mice belonging to the NMRI strain (body weight 20 to 25 g. both male and female) were used, 6 animals for each dose. The test compound was administered orally in a volume of 20 ml/kg, the maximum oral and intraperitoneal doses were 1000 mg/kg and 300 mg/kg, respectively. After treatment the animals were observed for a period of 7 days. The mice were kept under usual laboratory conditions. The toxicity data are summarized in Table I.

TABLE I

| Compound (No. of Example) | $LD_{50}$ (mg/kg, i.p.) | $LD_{50}$ (mg/kg, p.o.) |
|---|---|---|
| 2 | >300 | >1000 |
| 3 | >300 | >1000 |
| 4 | >300 | >1000 |
| 19 | >300 | >1000 |
| 5 | >300 | >1000 |
| 6 | >300 | >1000 |
| 7 | >300 | 1000 |
| 20 | >300 | >1000 |
| 21 | >300 | >1000 |
| 8 | >300 | >1000 |
| 9 | >300 | >1000 |
| Diazepam | >300 | 780[+] |

[+]literary data

II. Anxiolytic Activity

1. Vogel Test (Lick Conflict Test)

Male Wistar rats of 160 to 180 g body weight were kept free of food and drinking water for 24 and 48 hours, respectively. The test and carrier substances (0.4% methylcellulose) were administered orally one hour before testing. Groups consisting of 8 animals were used. The rats within the experimental chamber were provided with drinking water through an inserted tube. After the animals' each twenty lapping for water the device emitted a 1.4 mA intensity electric shock through the drinking tube. During 5 minutes the shocks tolerated by the animals in order to quench their thirst were counted. The effect of treatment was expressed as the % increase of the tolerated shocks. The minimum effective dose (MED) was determined for each test compound (Vogel, J. R., Beer, B., Clody, D. E.: Psychopharmacologia (Berl.) 21, 1 /1971/). The data obtained are summarized in Table II.

TABLE II

| Compound (No. of Example) | Minimum effective dose (mg/kg, p.o.) |
|---|---|
| 3 | 0,00001 |
| 4 | 0,01 |
| 5 | 0,0003 |
| 6 | 0,01 |
| 20 | 0,001 |
| 21 | 0,03 |
| 9 | 0,01 |
| Diazepam | 0,1 |

As it can be seen from the above Table, the anxiolytic activity of the compounds according to the invention is stronger by orders of magnitude than that of diazepam used as reference substance.

1.2 Elevated Plus Maze Test on Rat

The test was carried out with the aid of a wooden plus-shaped maze elevated to a height of 50 cm. Two arms (100 cm long and 15 cm wide)—opposite to one another—were enclosed up to a height of 40 cm along their longer sides and at the end. The other two arms were without walls (open arms). The central 15×15 cm part was open. Male rats belonging to the Sprague Dawley strain and weighing 220 to 260 g were used as test animals. After pretreatment lasting 60 minutes the animals were placed into the central part of the maze. During the 5 minutes observation period the following parameters were recorded:

time spent on the open arms time spent on the closed arms number of open arm entries number of closed arm entries.

The drug effect was expressed as percent increase of the time spent on the open arms and number of open arm entries. The minimum effective dose which caused a significant increase of the time spent on the open arms was calculated for every substance [Pelow, S., Chopin, P., File, S. E., Briley, M.: J. Neurocsi. Methods 14, 149–167 (1985)]. The data are shown in Table III.

TABLE III

| Compound (No. of Example) | Minimum effective dose (mg/kg, p.o.) |
|---|---|
| 3. | 0,1 |
| Diazepam | 2,5 |

The compound according to Example 3 proved to be 25 times more effective than diazepam.

3. Hole-Board Teszt

The experiment was carried out according to a slightly modified method of File [File, S. E., Wardill, A. G., Psychopharmacologia, 44, 53–59, (1975)]. Male Wistar rats (Charles River) weighing 160–200 g were fasted for 24 hours prior to the experiment. They were treated orally in a volume of 5 ml/kg one hour before testing, a treated group consisted of 12 animals. The test compounds were suspended in 0,4 methylcellulose solution, the control group was treated with methylcellulose. All procedures were carried out in a quiet, air-conditioned laboratory between 9:00 and 13:00 hours at ambient temperature (23°+2° C.). Locomotor and head-dipping activity were measured using automated test chambers (Digiscan, OMNITECH Electronics Inc., Columbus, Ohio). The floor of each box contained 4 equally spaced holes (3.5 cm in diameter) through which rat could pop its head. Interruptions of infrared beams (16 of them is located 1.0 cm below and an other 163.0 cm above the floor level) were automatically recorded by digiscan analyser and then transmitted to a computer and analysed by OASIS softwer. The hole-board testing involved placing a rat in the center of the floor and allowing it to explore for 5 minutes.

At the end of each trial any boluses were removed and the box was thoroughly wiped. Minimum effective doses of the compounds were calculated from the head-dipping activity values. The results are shown in Table IV.

TABLE IV

| Compound (No. of Example) | Minimum effective dose (mg/kg, p.o.) |
| --- | --- |
| 3 | 0,0001 |
| 6 | 0,0001 |
| 21 | 0,01 |
| Diazepam | 0,1 |

All the three test compounds proved to be more active than diazepam, one by one order of magnitude and two by three orders of magnitude.

According to a further aspect of the present invention there are provided pharmaceutical compositions comprising as active ingredient a compound of general formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatin capsule, solution, emulsion or suspension), parenteral (e.g. injection solution) or rectal (e.g. suppository) administration.

As carrier for the preparation of tablets, coated tablets, dragées and solid gelatin capsules e.g. lactose, corn starch, potato starch, talc, magnesium carbonate, magnesium stearate, calcium carbonate, stearic acid or the salts thereof, etc. can be used. As carrier for the soft gelatin capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers etc. The pharmaceutical formulations may further comprise other active ingredients, too.

The daily dose of the compounds of general formula (I) can vary within wide ranges depending on several factors, e.g. on the activity of the active ingredient, the patient's condition and age, the severity of the disease etc. The preferred oral dose is generally 0.1 to 200 mg/day. It has to be stressed that the above dose is only of informative character and the administered dose must always be determined by the physician therapeutist.

According to a further aspect of the present invention there is provided the use of the compounds of genreal formula (I) or pharmaceutically acceptable acid addition salts thereof for the preparation of pharmaceutical compositions having particularly anxiolytic properties.

According to a still further aspect of the present invention there is provided a method of anxiolytic treatment, which comprises administering to a patient an effective amount of a compound of general formula (I) or a pharmaceutically acceptable acid addition salt thereof.

Further details of the present invention are to be found in the following Examples without limiting the scope of protection to the said Examples.

EXAMPLE 1

(Method A)

A mixture of 20.4 g (0.1 mole) of 1-methyl-6,7-dimethoxyisoquinoline, 18.9 g (0.108 mole) of 2,6-dichlorobenzaldehyde and 15 ml of acetic anhydride is stirred in an oil bath of 150°–160° C. for 3 hours. The termination of the reaction is controlled by thin layer chromatography. The reaction mixture is cooled to a temperature between 5° C. and 10° C. under stirring, 30 ml of ether are added to it, the separated crystals are filtered and washed twice with cold ether. The thus-obtained raw product is recrystallized from a mixture of 600 ml of acetone and 130 ml of water, The clarified solution is stirred at a temperature between 0° C. and 5° C. for 2 hours, the separated substance is filtered, washed with 25 ml of a 6:1.3 mixture of 0° C. acetone and water and dried. Thus 28.4 g (79%) of 1-(2,6-dichlorostyryl)-6,7-dimethoxyisoquinoline are obtained.

M.p.: 145°–146° C. (acetone) Analysis for the formula $C_{19}H_{15}Cl_2NO_2$ (360.25): Calculated: C: 63.35, H: 4.20, N: 3.89, Cl: 19.68% Found: 62.87, 3.99, 3.95, 19.53% $^1$H-NMR (CDCl$_3$): δ 8.47 (1H, d, J=5.5), 7.98 (1H, d, J=16.0), 7.89 (1H, d, J=16.0), 7.46 (1H, s), 7.43 (1H, d, J=5.5), 7.37 (2H, d, J=8.0), 7.12 (1H, m), 7.03 (1H, s), 4.02 (3H, s), 4.00 (3H, s).

EXAMPLE 2

According to the method of Example 1 1-(4-chlorostyryl)-3-methyl-6,7-dimethoxyisoquinoline is prepared from 1,3-dimethyl-6,7-dimethoxyisoquinoline with 4-chlorobenzaldehyde. Yield: 51%.

M.p.: 181°–183° C. (ethyl acetate) Analysis for the formula $C_{20}H_{18}ClNO_2$ (339.83): Calculated: C: 70.69, H: 5.34, N: 4.12, Cl: 10.43% Found: 70.96, 5.33, 4.31, 10.41% $^1$H-NMR (CDCl$_3$): δ 7.86 (1H, d, J=15.5), 7.73 (1H, d, J=15.5), 7.56 (2H, d, J=8.5), 7.38 (1H, s). 7.34 (2H, d, J=8.5), 7.23 (1H, s), 6.92 (1H, s), 4.02 (3H, s), 3.98 (3H, s), 2.66 (3H, s).

EXAMPLE 3

According to the method of Example 1 6,7-methylenedioxy-1-[(4-trifluoromethyl)-styryl]-isoquinoline is prepared from 1-methyl-6,7-methylenedioxyisoquinoline with 4-(trifluoromethyl)-benzaldehyde. Yield: 66%.

M.p.: 143°–145° C. (methanol) Analysis for the formula $C_{19}H_{12}F_3NO_2$ (343.31): Calculated: C: 66.47, H: 3.52, N: 4.08% Found: 65.80, 3.51, 4.16% $^1$H-NMR (CDCl$_3$): δ 8.40 (1H, d, J=5.5), 7.92 (1H, d, J=15.6), 7.81 (1H, d, J=15.6), 7.72 (2H, d, J=8.3), 7.63 (2H, d J=8.3), 7.53 (1H, s), 7.40 (1H, d, J=5.5), 7.04 (1H, s), 6.09 (2H, s).

EXAMPLE 4

According to the method of Example 1 3-methyl-6,7-dimethoxy-1-(4-nitrostyryl)-isoquinoline is prepared from 1,3-dimethyl-6,7-dimethoxyisoquinoline with 4-nitrobenzaldehyde. Yield: 64%.

M.p.: 231°–232° C. (acetone:dioxane=2:1) Analysis for the formula $C_{20}H_{18}N_2O_4$ (350.38): Calculated: C: 68.56, H: 5.18, N: 8.00% Found: 68.96, 5.17, 8.09% $^1$H-NMR (CDCl$_3$): δ 8.26 (2H, d, J=9.0), 8.00 (1H, d, J=15.6), 7.93 (1H, d, J=15.6), 7.78 (2H, d, J=9.0), 7.43 (1H, s), 7.34 (1H, s), 7.00 (1H, s), 4.07 (3H, s), 4.03 (3H, s), 2.69 (3H, S)

EXAMPLE 5

According to the method of Example 1 1-(4-fluorostyryl)-6,7-dimethoxyisoquinoline is prepared from 1-methyl-6,7-dimethoxyisoquinoline with 4-fluorobenzaldehyde. Yield: 51%). M.p.: 169°–171° C. (acetone) Analysis for the formula $C_{19}H_{16}FNO_2$ (309.35): Calculated: C: 73.77, H: 5.21, N: 4.53% Found: 72.91, 4.92, 4.75% $^1$H-NMR (CDCl$_3$): δ 8.42 (1H, d, J=5.5), 7.90 (1H, d, J=15.5), 7.89 (1H, d, J=15.5), 7.67 (2H, m), 7.44 (1H, s), 7.40 (1H, d, J=5.5), 7.08 (2H, m), 7.02 (1H, s), 4.05 (3H, s), 4.01 (3H, s).

EXAMPLE 6

According to the method of Example 1 6,7-dimethoxy-1-[4-(trifluoromethyl)-styryl]-isoquinoline is prepared from 1-methyl-6,7-dimethoxyisoquinoline with 4-trifluoromethylbenzaldehyde. Yield: 57%.

M.p.: 146°–148° C. (acetone) Analysis for the formula $C_{20}H_{16}F_3NO_2$ (359.36): Calculated: C: 66.85, H: 4.49, N: 3.90% Found: 65.16, 5.01, 3.73% $^1$H-NMR (CDCl$_3$): δ 8.44 (1H, d, J=5.6), 7.95 (1H, d, J=15.5), 7.86 (1H, d, J=15.5), 7.73 (2H, d, J=8.3), 7.63 (2H, d, J=8.3), 7.44 (1H, d, J=5.6), 7.43 (1H, s), 7.04 (1H, s), 4.06 (3H, s), 4.01 (3H, s).

EXAMPLE 7

According to the method of Example 1 1-(3,4-dimethoxystyryl)-6,7-dimethoxyisoquinoline is prepared from 1-methyl-6,7-dimethoxyisoquinoline with 3,4-dimethoxybenzaldehyde. Yield 54%.

M.p.: 136°–138° C. (acetone) Analysis for the formula $C_{21}H_{21}NO_4$ (351.41): Calculated: C: 71.78, H: 6.02, N: 3.99% Found: 71.56, 6.00, 4.05% $^1$H-NMR (CDCl$_3$): δ 8.42 (1H, d, J=5.5), 7.89 (1H, d, J=15.5), 7.68 (1H, d, J=15.5), 7.50 (1H, s), 7.40 (1H, d, J=5.5), 7.28 (1H, dd, J=8.3, 1.9), 7.20 (1H, d, J=1.9), 7.04 (1H, s), 6.91 (1H, d, J=8.3), 4.07 (3H, s), 4.02 (3H, s), 3.96 (3H, s), 3.92 (3H, s).

EXAMPLE 8

According to the method of Example 1 1-(2,4-dichlorostyryl)-isoquinoline is prepared from 1-methylisoquinoline with 2,4-dichlorobenzaldehyde. Yield 53%.

M.p.: 188°–190° C. (dioxane) Analysis for the formula $C_{17}H_{11}Cl_2N$ (312.21): Calculated: C: 69.25, H: 3.55, N: 4.49, Cl: 22.71% Found: 68.04, 3.63, 4.61, 22.91%. $^1$H-NMR (CDCl$_3$): δ 8.59 (1H, d, J=5.7), 8.33 (1H, d, J=8.5), 8.26 (1H, d, J=15.6), 7.95 (1H, d, J=15.6), 7.80–7.20 (7H, m).

EXAMPLE 9

According to the method of Example 1 1-(4-cyanostyryl)-3-methyl-6,7,8-trimethoxyisoquinoline is prepared from 1,3-dimethyl-6,7,8-trimethoxyisoquinoline with 4-cyanobenzaldehyde. Yield: 69%.

M.p.: 177°–180.5° C. (acetone) Analysis for the formula $C_{22}H_{20}N_2O_3$ (360.42) Calculated: C: 73.32, H: 5.59, N: 7.77% Found: 72.36, 5.59, 7.99% $^1$H-NMR (CDCl$_3$): δ 8.61 (1H, d, J=15.7), 7.73 (1H, d, J=15.7), 7.72 (2H, d, J=8.5), 7.64 (2H, d, J=8.5), 7.29 (1H, s), 6.83 (1H, s), 4.00 (6H, s), 3.94 (3H, s), 2.67 (3H, s).

EXAMPLE 10

According to the method of Example 1 1-(2-fluorostyryl)-3-methyl-6,7-dimethoxyisoquinoline is prepared from 1,3-dimethyl-6,7-dimethoxyisoquinoline with 4-fluorobenzaldehyde. Yield: 54%

M.p.: 138°–139.5° C. (ethyl acetate) Analysis for the formula $C_{20}H_{18}FNO_2$ (323.37): Calculated: C: 74.29, H: 5.61, N: 4.33, F: 5.87% Found: 74.14, 5.56, 4.25, 6.02% $^1$H-NMR (CDCl$_3$): δ 8.00 (1H, d, J=15.8), 7.91 (1H, d, J=15.8), 7.73 (1H, m), 7.45 (1H, s), 7.27 (1H, s), 7.35–7.10 (3H, m), 6.95 (1H, s), 4.04 (3H, s), 4.00 (3H, s) 2.68 (3H, s).

EXAMPLE 11

According to the method of Example 1 6,7-dimethoxy-1-(3-methoxystyryl)-isoquinoline is prepared from 1-methyl-6,7-dimethoxyisoquinoline with 3-methoxybenzaldehyde. Yield 54%.

M.p.: 129°–130° C. (methanol) Analysis for the formula $C_{20}H_{19}NO_3$ (321.39): Calculated: C: 74.75, H: 5.96, N: 4.36%, Found: 74.61, 5.80, 4.39%. $^1$H-NMR (CDCl$_3$): δ 8.42 (1H, d, J=5.5), 7.91 (1H, d, J=15.6), 7.79 (1H, d, J=15.6), 7.47 (1H, s), 7.41 (1H, d, J=5.5), 7.40 7.25 (3H, m), 7.03 (1H, s), 6.88 (1H, m), 4.06 (3H, s), 4.01 (3H, s), 3.86 (3H, s).

EXAMPLE 12

According to the method of Example 1 6,7-dimethoxy-1-(3,4,5-trimethoxystyryl)-isoquinoline is prepared from 1-methyl-6,7-dimethoxyisoquinoline with 3,4,5-trimethoxybenzaldehyde. Yield: 64%.

M.p.: 144°–145.5° C. (isopropanol) Analysis for the formula $C_{22}H_{23}NO_5$ (381.44): Calculated: C: 69.28, H 6.08, N: 3.67% Found: 67.70, 6.34, 3.83% $^1$H-NMR (CDCl$_3$): δ 8.42 (1H, d, J=5.5), 7.86 (1H, d, J=15.5), 7.68 (1H, d, J=15.5), 7.49 (1H, s), 7.42 (1H, d, J=5.5), 7.06 (1H, s), 6.90 (2H, s), 4.07 (3H, s), 4.03 (3H, s), 3.94 (6H, s), 3.90 (3H, s).

EXAMPLE 13

According to the method of Example 1 1-(3-bromostyryl)-6,7-dimethoxyisoquinoline is prepared from 1-methyl-6,7-dimethoxyisoquinoline with 3-bromobenzaldehyde. Yield: 58%.

M.p.: 162°–164° C. (acetone) Analysis for the formula $C_{19}H_{16}BrNO_2$ (370.26): Calculated: C: 61.64, H: 4.36, N: 3.78, Br: 21.58% Found: 61.27, 4.32, 3.71, 21.50% $^1$H-NMR (CDCl$_3$): δ 8.40 (1H, d, J=5.5), 7.84 (1H, d, J=15.5), 7.79 7.73 (1H, d, J=15.5), (1H, t, J=1.6), 7.60, 7.20 (3H, m), 7.40 7.29 (1H, d, J=5.5), (1H, s), 6.99 (1H, s), 4.05 (3H, s), 3.98 (3H, s).

EXAMPLE 14

According to the method of Example 1 6,7-dimethoxy-1-[2-(2-pyridinyl)-ethenyl]-isoquinoline is prepared from 1-methyl-6,7-dimethoxyisoquinoline with pyridine-2-carbaldehyde. Yield: 54%.

M.p.: 173°–175° C. (ethanol) Analysis for the formula $C_{18}H_{16}N_2O_2\times 2H_2O$ (328.38): Calculated: C: 65.84, H: 6.14, N: 8.53% Found: 66.17, 6.07, 8.63% $^1$H-NMR (CDCl$_3$): δ 8.67 (1H, dd, J=4.60, 1.30), 8.53 (1H, d, J=15.1),8.44 7.95 (1H, d, J=15.1), (1H, d, J=5.5), (1H, d, J=5.5), 7.73–7.66 (1H, m), 7.65 (1H, s), 7.46–7.41 (1H, m), 7.44 7.23–7.17 (1H, m), 7.04 (1H, s), 4.09 (3H, s), 4.01 (3H, s)

EXAMPLE 15

According to the method of Example 1 1-(2-nitrostyryl)-isoquinoline is prepared from 1-met-methylisoquinoline with 2-nitrobenzaldehyde. Yield 51%. M.p.: 156°–160° C. (acetone) Analysis for the formula $C_{17}H_{12}N_2O_2$ (276.30): Calculated: C: 73.90, H: 4.38, N: 10.14% Found: 73.44, 4.35, 10.04% $^1$H-NMR (CDCl$_3$): δ 8.57 (1H, d, J=5.5), 8.33 (1H, d, J=15.3), 8.32 (1H, m), (7H, m) 7.89 (1H, d, J=15.3), 7.60 (1H, d, J=5.5), 8.00–7.50.

EXAMPLE 16

According to the method of Example 1 6,7,8-trimethoxy-1-(3-nitrostyryl)-isoquinoline is prepared from 1 methyl-6,7,8-trimethoxyisoquinoline with 3-nitrobenzaldehyde. Yield: 56%.

M.p.: 1.49°–154° C. (diisopropyl ether:ethanol—5:1) Analysis for the formula $C_{20}H_{18}N_2O_5$ (366.30): Calculated: C: 65.57, H: 4.95, N: 7.65% Found: 65.05, 4.90, 7.70% $^1$H-NMR (CDCl$_3$): δ 8.64 (1H, d, J=15.7), 8.51 (1H, t, J=1.9), 8.43 (1H, d, J=5.6), 8.12 (1H, m), 7.93 (1H, d, J=7.9), 7.76 (1H, d, J=15.7), 7.55 (1H, t, J=7.9), 7.44 (1H, d, J=5.6), 6.93 (1H, s), 4.03 (3H, s), 4.01 (3H, s), 3.99 (3H, s).

EXAMPLE 17

According to the method of Example 1 1-(4-bromostyryl)-6,7,8-trimethoxyisoquinoline is prepared from 1-methyl-6,7,8-trimethoxyisoquinoline with 4-bromobenzaldehyde. Yield: 56%.

M.p.: 115°–117° C. (acetone: ethanol=7:1) Analysis for the formula $C_{20}H_{18}BrNO_3$ (400.28): Calculated: C: 60.01, H: 4.53, N: 3.49, Br: 19.96% Found: 59.84, 4.61, 3.32, 20.01% $^1$H-NMR (CDCl$_3$): δ 8.51 (1H, d, J=15.7), 8.41 (1H, d, J=5.5), 7.67 (1H, d, J=15.7), 7.52 (4H, m), 7.41 (1H, d, J=5.5), 6.91 (1H, s), 4.01 (6H, s), 3.94 (3H, s).

EXAMPLE 18

According to the method of Example 1 3-methyl-6,7-methylenedioxy-1-[2-(2-thienyl)-ethenyl]-isoquinoline is prepared from 1,3-dimethyl-6,7-methylenedioxyisoquinoline with thiophen-2-carbaldehyde. Yield 61%.

M.p.: 163°–166° C. (Ethyl acetate: n-heptane=5:2) Analysis for the formula $C_{17}H_{13}NO_2S$ (295.37): Calculated: C: 69.13, H: 4.44, N: 4.74, S: 10.86%, Found: 69.28, 4.53, 4.77, 10.85% $^1$H-NMR (CDCl$_3$): δ 8.02 (1H, d, J=15.3), 7.49 (1H, d, J=15.3), 7.41 (1H, s), 7.25 (2H, m), 7.13 (1H, s), 7.05 (1H, m), 6.86 (1H, s), 5.98 (2H, s), 2.61 (3H, s).

EXAMPLE 19

According to the method of Example 1 1-(3-bromostyryl)-3-methyl-6,7-methylenedioxyisoquinoline is prepared from 1,3-dimethyl-6,7-methylenedioxyisoquinoline with 3-bromobenzaldehyde. Yield 53%.

M.p.189°–190° C. (acetone) Analysis for the formula $C_{19}H_{14}BrNO_2$ (368.24): Calculated: C: 61.97, H: 3.83, N: 3.80, Br: 21.70%, Found: 61.70, 3.87, 3.84, 21.32%. $^1$H-NMR (CDCl$_3$): δ 7.81 (1H, d, J=15.5), 7.81 7.76 (1H, d, J=15.5), (1H, m), 7.56–7.40 (3H, m), 7.28–7.21 (2H, m), 6.96 (1H, s), 6.07 (2H, s), 2.65 (3H, s).

EXAMPLE 20

According to the method of Example 1 1-(3,4-dimethoxystyryl)-6,7-methylenedioxyisoquinoline is prepared from 1-methyl-6,7-methylenedioxyisoquinoline with 3,4-dimethoxybenzaldehyde. Yield 55%.

M.p.: 204°–207° C. (Ethanol:dichloroethane=6.5:1.0) Analysis for the formula $C_{20}H_{17}NO_4$ (335.37): Calculated: C: 71.63, H: 5.11, N: 4.18%, Found: 70.08, 5.24, 4.26%. $^1$H-NMR (CDCl$_3$): δ 8.40 (1H, d, J=5.5), 7.87 (1H, d, J=15.5), 7.64 (1H, d, J=15.5), 7.62 (1H, s), 7.38 (1H, d, J=5.5), 7.27–7.21 (2H, m), 7.08 (1H, s), 6.91 (1H, d, J=8.0), 6.12 (2H, s), 3.98 (3H, s), 3.93 (3H, s).

EXAMPLE 21

According to the method of Example 1 6,7-dimethoxy-1-(4-methoxystyryl)-isoquinoline is prepared from 1-methyl-6,7-dimethoxyisoquinoline with 4-methoxybenzaldehyde. Yield 52%.

M.p.: 146°–150° C. (acetone) Analysis for the formula $C_{20}H_{19}NO_3$ (321.39): Calculated: C: 74.75, H: 5.96, N: 4.36% Found 76.15, 5.89, 4.43% $^1$H-NMR (CDCl$_3$): δ 8.41 (1H, d, J=5.5), 7.90 (1H, d, J=15.5), 7.70 (1H, d, J=15.5), 7.63 (2H, d, J=8.7), 7.50 (1H, s), 7.39 (1H, d, J=5.5), 7.04 (1H, s), 6.95 (2H, d, J=8.7), 4.07 (3H, s), 4.02 (3H, s), 3.84 (3H, s).

EXAMPLE 22

According to the method of Example 1 1-(3,4-dimethoxystyryl)-3-methyl-6,7-dimethoxyisoquinoline is prepared from 1,3-dimethyl-6,7-dimethoxyisoquinoline with 3,4-dimethoxybenzaldehyde. Yield 68%. M.p.: 139.5°–140.5° C. (acetone-water 1:1) Analysis for the formula $C_{22}H_{23}NO_4$ (365.44): Calculated: C: 72.31, H: 6.31, N: 3.83% Found: 72.46, 6.45, 3.68% $^1$H-NMR (CDCl$_3$): δ 7.86 (1H, d, J=15.5), 7.66 (1H, d, J=15.5), 7.47 (1H, s), 7.29–7.24 (2H, m), 7.20 (1H, d, J=1.9), 6.95 (1H, s), 6.90 (1H, d, J=8.3), 4.04 (3H, s), 4.00 (3H, s), 3.96 (3H, s), 3.91 (3H, s), 2.67 (3H, s).

EXAMPLE 23

According to the method of Example 1 1-(3,4-dichlorostyryl)-3-methyl-6,7-dimethoxyisoquinoline is prepared from 1,3-dimethyl-6,7-dimethoxyisoquinoline with 3,4-dichlorobenzaldehyde. Yield 51%). M.p.: 154°–156° C. (acetone-water) Analysis for the formula $C_{20}H_{17}Cl_2NO_2$ (374.28): Calculated: C: 64.19, H: 4.58, N: 3.74, Cl: 18.94% Found: 64.96, 4.53, 3.65, 19.07% $^1$H-NMR (CDCl$_3$): δ 7.83 (1H, d, J=15.5), 7.74 (1H, d, J=15.5), 7.73 (1H, s), 7.44 (2H, s), 7.40 (1H, s), 7.29 (1H, s), 6.96 (1H, s), 4.06 (3H, s), 4.01 (3H, s), 2.67 (3H, s)

EXAMPLE 24

According to the method of Example 1 1-(2-bromostyryl)-6,7-dimethoxyisoquinoline is prepared from 1-methyl-6,7-dimethoxyisoquinoline with 2-bromobenzaldehyde. Yield 69%.

M.p.. 181°–182° C. (acetone) Analysis for the formula $C_{19}H_{16}BrNO_2$ (370.26): Calculated: C: 61.64, H: 4.36, N: 3.78, Br: 21.58% Found: 61.20, 4.29, 7.76, 21.39% $^1$H-NMR (CDCl$_3$): δ 8.44 (1H, d, J=5.5), 8.18 (1H, d, J=15.5),7.85–7.70 (1H, d, J=15.5), 7.15 (4H, m), 7.46 (1H, s), 7.40 (1H, d, J=5.5), 7.01 (1H, s), 4.03 (3H, s), 3.99 (3H, s).

EXAMPLE 25

According to the method of Example 1 6,7-methylenedioxy-1-(3,4-methylenedioxystyryl)-isoquinoline is prepared from 1-methyl-6,7-methylenedioxyisoquinoline with 3,4-methylenedioxybenzaldehyde. Yield 58%. M.p.: 184°–188° C. (Ethylacetate: methanol=4:1) Analysis for the formula $C_{19}H_{13}NO_4$ (319.33): Calculated: C: 71.47, H: 4.10, N: 4.39%, Found: 71.05, 4.13, 4.37%. $^1$H-NMR (CDCl$_3$): δ 8.38 (1H, d, J=5.5), 7.83 (1H, d, J=15.5), 7.59 (1H, d, J=15.5), 7.56 (1H, s), 7.36 (1H, d, J=5.5), 7.21 (1H, d, J=1.4), 7.11 (1H, dd, J=8.1, 1.4), 7.04 (1H, s), 6.83 (1H, d, J=8.1), 6.08 (2H, s), 6.00 (2H, s).

EXAMPLE 26

According to the method of Example 1 1-(2-chlorostyryl)-6,7,8-trimethoxyisoquinoline is prepared from 1-methyl-6,7,8-trimethoxyisoquinoline with 2-chlorobenzaldehyde. Yield 59%.

M.p.: 120°–123° C. (methanol) Analysis for the formula $C_{20}H_{18}ClNO_3$ (355.83): Calculated: C: 67.51, H: 5.10, N: 3.94, Cl: 9.96%, Found: 67.25, 5.19, 3.98, 9.83%. $^1$H-NMR (CDCl$_3$): δ 8.49 (1H, d, J=15.7), 8.44 (1H, d, J=5.4), 8.12 (1H, d, J=15.7), 7.85, (1H, d, J=7.6, 1.8,), 7.41 (1H, d, J=1.6), 7.40 (1H, d, J=5.4), 7.40–7.20 (2H, m), 6.90 (1H, s), 4.00 (3H, s), 3.99 (3H, s), 3.93 (3H, s).

EXAMPLE 27

According to the method of Example 1 1-(4-dimethylaminostyryl)-3-methyl-6,7-methylenedioxyisoquinoline is prepared from 1,3-dimethyl-6,7-methylenedioxyisoquinoline with 4-dimethylaminobenzaldehyde. Yield 51%. M.p.:

183°–187° C. (acetone) Analysis for the formula C$_{21}$H$_{20}$N$_2$O$_2$ (332.41): Calculated: C: 75.88, H: 6.06, N: 8.43% Found: 75.70, 6.03, 8.51% $^1$H-NMR (CDCl$_3$): δ 7.84 (1H, d, J=15.5), 7.56 (1H, d, J=15.5), 7.56 (2H, d, J=8.8), 7.55 (1H, s), 7.25 (1H, s), 6.94 (1H, s), 6.73 (2H, d, J=8.8), 6.05 (2H, s), 3.00 (6H, s), 2.65 (3H, s).

EXAMPLE 28

According to the method of Example 1 1-(3-chlorostyryl)-6,7-dimethoxyisoquinoline is prepared from 1-methyl-6,7-dimethoxyisoquinoline with 3-chlorobenzaldehyde. Yield: 52%.

M.p.: 161°–162° C. (ethanol) Analysis for the formula C$_{19}$H$_{16}$ClNO$_2$ (325.80): Calculated: C: 70.05, H: 4.95, N: 4.30, Cl: 10.88% Found: 69.64, 4.82, 4.38, 10.88% $^1$H-NMR (CDCl$_3$): δ 8.42 (1H, d, J=5.4), 7.88 (1H, d, J=15.5), 7.78 (1H, d, J=15.5), 7.65 (1H, s). 7.55– 7.25 (5H, m), 7.04 (1H, s), 4.08 (3H, s), 4.01 (3H, s).

EXAMPLE 29

(Method B)

A mixture of 6.44 g (0.045 mole) of 1-methylisoquinoline, 6.2 g (0.05 mole) of 3-fluorobenzaldehyde and 18 ml of acetic acid is stirred at a temperature between 130° C. and 140° C. for 3 hours. The termination of the reaction is controlled by thin layer chromatography. The reaction mixture is cooled and 100 ml of anhydrous acetone are added to it. Then it is acidified with a mixture of hydrogen chloride and isopropanol until pH=1 under stirring and cooling with ice-water. The suspension is stirred at a temperature between 0° C. and 5° C. for 2 hours. The separated hydrogen chloride salt is filtered, washed with cold acetone and dissolved in 180 ml of water. To the thus-obtained mixture 20% sodium hydroxide solution is dropped until pH=11–12 under stirring and cooling with ice-water, and the solution is extracted three times with 75 ml each of dichloromethane. The extracts are combined, washed with an aqueous sodium chloride solution, dried over Na$_2$SO$_4$ and evaporated. The crude product is recrystallized from 30 ml of isopropanol. Thus 8.7 g (78%) of 1-(3-fluorostyryl)-isoquinoline are obtained.

M.p.: 89°–99° C. (isopropanol) Analysis for the formula C$_{17}$H$_{12}$FN (249.30): Calculated: C: 81.91, H: 4.85, N: 5.62% Found: 81.45, 4.94, 5.72% $^1$H-NMR (CDCl$_3$): δ 8.55 (1H, d, J=5.6), 8.33 (1H, d, J=8.2), 7.99 (1H, d, J=16.0), 7.91 (1H, d, J=16.0), 7.80–6.95 (8H, m).

EXAMPLE 30

According to the method of Example 29 1-[2-(2-furyl)ethenyl]-6,7-dimethoxyisoquinoline is prepared from 1-methyl-6,7-dimethoxyisoquinoline and 2-furylcarbaldehyde. Yield: 51%. M.p.: 185°–190° C. (ethanol-water=9:1) Analysis for the formula C$_{17}$H$_{15}$NO$_3$ (281.32): Calculated: C: 72.58, H: 5.37, N: 4.98%, Found: 72.87, 5.29, 5.10%. $^1$H-NMR (CDCl$_3$): δ 8.37 (1H, d, J=5.5), 7.78 (1H, d, J=15.3), 7.71 (1H, d, J=15.3), 7.47 (1H, d, J=1.6), 7.43 (1H, s), 7.34 (1H, d, J=5.5), 6.96 (1H, s) 6.55–6.45 (2H, m), 4.04 (3H, s), 3.97 (3H, s).

EXAMPLE 31

According to the method of Example 29 1-(4-hydroxy-3-methoxystyryl)-isoquinoline is prepared from 1-methylisoquinoline with 3-methoxy-4-hydroxybenzaldehyde. Yield: 50%.

M.p.: 190°–230° C. [decomp.] (ethanol: water=10:1) Analysis for the formula C$_{18}$H$_{15}$NO$_2$×HCl (313.79): Calculated: C: 68.90, H: 5.14, N: 4.46, Cl: 11.30% Found: 66.34, 5.35, 4.56, 11.03% $^1$H-NMR (DMSO): δ 9.06 (1H, d, J=8.6), 8.46–8.39 (2H, m), 8.27–8.00 (5H, m), 7.64 (1H, d, J=1.7), 7.30 (1H, m), 6.97 (1H, d, J=8.1), 3.95 (3H, s).

EXAMPLE 32

According to the method of Example 1 (3,4-methylenedioxystyryl)-6,7-dimethoxy-1-isoquinoline is prepared from 1-methyl-6,7-dimethoxyisoquinoline and 3,4-methylenedioxybenzaldehyde. Yield: 63%

M.p.: 164°–166° C. (methanol) Analysis for the formula: C$_{20}$H$_{17}$NO$_4$ (335.37) Calculated: C: 71.63, H: 5.11, N: 4.18%, Found: 71.41, 5.07, 4.14%. $^1$H-NMR (CDCl$_3$): δ 8.38 (1H, d, J=5.4), 7.85 (1H, d, J=15.4), 7.61 (1H, d, J=15.4), 7.41 (1H, s), 7.35 (1H, d, J=5.5), 7.21 (1H, d, J=1.6), 7.10 (1H, dd, J=8.1, 1.6), 6.98 (1H, s), 6.82 (1H, d, J=8.1), 5.97 (2H, s), 4.03 (3H, s), 3.98 (3H, s).

EXAMPLE 33

According to the method of Example 1 3-methyl-6,7,8-trimethoxy-1-[2-(3-pyridinil)-ethenyl]-isoquinoline is prepared from 1,3-dimethyl-6,7,8-trimethoxyisoquinoline with pyridine-3-carbaldehyde. Yield 51%. M.p.: 93°–95° C. (diisopropyl ether) Analysis for the formula C$_{20}$H$_{20}$N$_2$O$_3$ (336.40): Calculated: C: 71.41, H: 5.99, N: 8.33% Found: 71.32, 6.00, 8.27% $^1$H-NMR (CDCl$_3$): δ 8.90 (1H, d, J=1.9), 8.58 (1H, d, J=15.7), 8.51 (1H, dd, J=4.7, 1.4), 7.96 (1H, d, J=8.0), 7.73 (1H, d, J=15.7), 7.30 (1H, dd, J=7.9, 4.8), 7.25 (1H, s), 6.80 (1H, s), 3.99 (3H, s), 3.97 (3H, s), 3.95 (3H, s), 2.67 (3H, s).

EXAMPLE 34

According to the method of Example 1 1-(2,5-dimethoxystyryl)-3-methyl-6,7,8-trimethoxyisoquinoline is prepared from 1,3-dimethyl-6,7,8-trimethoxyisoquinoline with 2,5-dimethoxybenzaldehyde. Yield 54%.

M.p.: 102°–110° C. (isopropanol) Analysis for the formula C$_{23}$H$_{25}$NO$_5$ (395.47): Calculated: C: 69.86, H: 6,37, N: 3.54% Found: 69.79, 6.33, 3.63% $^1$H-NMR (CDCl$_3$); δ 8.53 (1H, d, J=15.8), 8.13 (1H, d, J=15.8), 7.31 (1H, d, J=2.4), 7.19 (1H, s), 6.83 (2H, m), 6.76 (1H, s), 3.97 (3H, s), 3.95 (3H, s), 3.93 (3H, s), 3.91 (3H, s), 3.90 (3H, s), 2.66 (3H, s).

EXAMPLE 35

According to the method of Example 1 3-methyl-6,7,8-trimethoxy-1-[2-(1-naphtyl)-ethenyl]-isoquinoline is prepared from 1,3-dimethyl-6,7,8-trimethoxyisoquinoline with 1-naphtaldehyde. Yield 54%.

M.p.: 99°–106.5° C. (methanol) Analysis for the formula C$_{25}$H$_{23}$NO$_3$ (385.48): Calculated: C: 77.90, H: 6.01, N: 3.63% Found: 79.29, 6.32, 3.81% $^1$H-NMR (CDCl$_3$): δ 8.62 (1H, d, J=15.3), 8.56 (1H, d, J=15.3), 8.43 (1H, d, J=7.3), 7.96 (1H, d, J=6.6), 7.80 (2H, m), 7.50 (3H, m), 7.21 (1H, s), 6.75 (1H, s), 3.96 (3H, s), 3.91, 3.90 (3H, s), (3H, s), 2.70 (3H, s).

EXAMPLE 36

According to the method of Example 1 3-methyl-1-(3,4-methylenedioxy-2-methoxystyryl)-6,7,8-trimethoxyisoquinoline is prepared from 1,3-dimethyl-6,7,8-trimethoxyisoquinoline with 2-methoxy-3,4-methylenedioxybenzaldehyde. Yield 51%.

M.p.: 110°–115° C. (n-heptane: ethyl acetate=12: 5) Analysis for the formula C$_{23}$H$_{23}$NO$_6$ (409.45): Calculated: C: 67.47, H: 5.66, N: 3.42% Found: 67.00, 5.70, 3.49% $^1$H-NMR (CDCl$_3$): δ 8.45 (1H, d, J=15.7), 7.92 (1H, d, J=15.7), 7.25 (1H, d, J=8.2), 7.19 (1H, s), 6.78 (1H, s), 6.59

(1H, d, J=8.2), 5.96 (2H, s), 4.08 (3H, s), 3.97 (3H, s), 3.96 (3H, s), 3.92 (3H, s), 2.65 (3H, s).

EXAMPLE 37

According to the method of Example 1 6,7,8-trimethoxy-1-styryl)-isoquinoline is prepared from 1-methyl-6,7,8-trimethoxyisoquinoline with benzaldehyde. Yield 53%.

M.p.: 86°–88.5° C. (water: ethanol=3:1) Analysis for the formula $C_{20}H_{19}NO_3$ (321.38): Calculated: C: 74.75, H: 5.96, N: 4.36% Found: 74.60, 5.93, 4.38% $^1$H-NMR (CDCl$_3$): δ 8.54 (1H, d, J=15.7), 8.42 (1H, d, J=5.5), 7.76 (1H, d, J=15.7), 7.75–7.25 (5H, m), 7.39 (1H, d, J=5.5), 6.90 (1H, s), 4.01 (3H, s), 3.99 (3H, s), 3.95 (3H, s).

EXAMPLE 38

According to the method of Example 1 6,7,8-trimethoxy-1 -(3,4,5-trimethoxystyryl)-isoquinoline is prepared from 1-methyl-6,7,8-trimethoxyisoquinoline with 3,4,5-trimethoxybenzaldehyde. Yield 51%.

M.p.: 117.5°–125.5° C. (water: ethanol=4:1.5) Analysis for the formula $C_{23}H_{25}NO_6$ (411.47): Calculated: C: 67.14, H: 6.12, N: 3.40% Found: 66.95, 6.05, 3.47% $^1$H-NMR (CDCl$_3$): δ 8.45 (1H, d, J=15.6), 8.42, 7.69 (1H, d, J=15.6), (1H, d, J=5.6), 7.39 (1H, d, J=5.6), 6.93 (2H, s), 6.92 (1H, s), 4.02 (6H, s), 3.98 (3H, s), 3.93 (6H, s), 3.89 (3H, s).

What we claim is:

1. A method of anxiolytic treatment, which comprises administering to a patient suffering from anxiety a therapeutically effective amount of a pharmaceutical composition comprising;

1-styrylisoquinoline derivatives of formula (I)

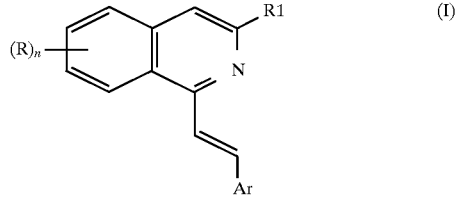

and pharmaceutically acceptable acid addition salts thereof, wherein n is 1, 2, 3 or 4, R may be the same or different and represent(s) hydrogen, lower alkyl, lower alkoxy or hydroxy, or two substituents R attached to adjacent carbon atoms may form together an alkylenedioxy group;

R1 represents hydrogen or lower alkyl, and

Ar stands for an optionally subtituted aryl or heteroaryl, wherein the substituents are selected from one or more identical or different substituent(s) selected from the group consisting of halogen, trihalomethyl, hydroxy, lower alkyl, lower alkoxy, lower alkylenedioxy, cyano, nitro, amino, mono- and di-(lower alkyl)-amino and further comprising a suitable solid or liquid pharmaceutical carrier.

2. A method of anxiolytic treatment, which comprises administering to a patient suffering from anxiety an effective amount of a pharmaceutical composition comprising;

1-styrylisoquinoline derivatives of formula (IA)

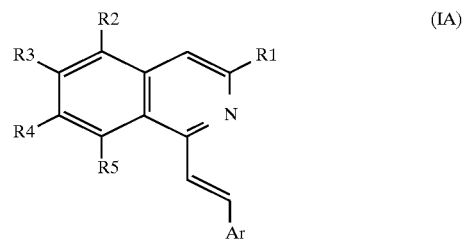

and pharmaceutically acceptable acid addition salts thereof, wherein

R1 stands for hydrogen or lower alkyl;

R2 represents hydrogen;

R3 and R4 each represent hydrogen or lower alkoxy, or together form a lower alkylenedioxy group, R5 represents hydrogen or lower alkoxy, and Ar denotes phenyl optionally carrying one or more identical or different substituent(s) selected from the group consisting of halogen, trihalomethyl, hydroxy, lower alkyl, lower alkoxy, lower alkylenedioxy, cyano, nitro, amino, mono- and di-lower alkyl amino, or naphtyl optionally carrying the above-mentioned substituents, or mono- or bicyclic heteroaryl, optionally carrying the above substituents and containing one or two oxygen, nitrogen and/or sulfur atom(s) and further comprising a suitable solid or liquid pharmaceutical carrier.

* * * * *